(12) United States Patent
Chen et al.

(10) Patent No.: US 10,338,011 B2
(45) Date of Patent: *Jul. 2, 2019

(54) MULTI-MODALITY DETECTION SYSTEM AND METHOD

(71) Applicants: TSINGHUA UNIVERSITY, Beijing (CN); NUCTECH COMPANY LIMITED, Beijing (CN)

(72) Inventors: Zhiqiang Chen, Beijing (CN); Li Zhang, Beijing (CN); Tianyi Yang Dai, Beijing (CN); Qingping Huang, Beijing (CN); Yunda Sun, Beijing (CN); Xin Jin, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 231 days.

This patent is subject to a terminal disclaimer.

(21) Appl. No.: 15/263,207

(22) Filed: Sep. 12, 2016

(65) Prior Publication Data

US 2017/0176353 A1 Jun. 22, 2017

(30) Foreign Application Priority Data

Dec. 18, 2015 (CN) .......................... 2015 1 0958891

(51) Int. Cl.
*G01N 23/046* (2018.01)
*G01N 23/083* (2018.01)
(Continued)

(52) U.S. Cl.
CPC ......... *G01N 23/046* (2013.01); *G01N 23/083* (2013.01); *G01N 23/207* (2013.01);
(Continued)

(58) Field of Classification Search
CPC ....... G01N 2223/056; G01N 2223/316; G01N 2223/419; G01N 2223/643; G01N 23/046;
(Continued)

(56) References Cited

U.S. PATENT DOCUMENTS 7,486,760 B2 * 2/2009 Harding ................. G01N 23/20
378/7
7,787,591 B2 8/2010 Harding et al.
(Continued)

FOREIGN PATENT DOCUMENTS

CN 1898581 1/2007
CN 101617247 12/2009
(Continued)

OTHER PUBLICATIONS

Extended Search Report dated Apr. 11, 2017 in EP Application No. 16185367.6 (10 pages).
(Continued)

*Primary Examiner* — Irakli Kiknadze
(74) *Attorney, Agent, or Firm* — Knobbe, Martens, Olson & Bear LLP

(57) ABSTRACT

The present disclosure relates to multi-modality detection systems and methods. One illustrative multi-modality detection system may include a distributed radiation source configured to irradiate an object under detection, a primary collimator configured to separate rays of the distributed radiation source into two parts, wherein one part is for CT detection and the other part is for XRD detection, a CT detection device configured to perform a CT detection to acquire a CT image of the object under detection, and an XRD detection device configured to perform an XRD detec-
(Continued)

tion to acquire an XRD image of the object under detection, wherein the CT detection and the XRD detection are performed simultaneously.

19 Claims, 7 Drawing Sheets

(51) Int. Cl.
    *G01N 23/207* (2018.01)
    *G21K 1/02* (2006.01)
    *G01N 23/20* (2018.01)
    *G01V 5/00* (2006.01)

(52) U.S. Cl.
    CPC ....... *G01N 23/20083* (2013.01); *G01V 5/005* (2013.01); *G21K 1/02* (2013.01); *G01N 2223/056* (2013.01); *G01N 2223/316* (2013.01); *G01N 2223/419* (2013.01); *G01N 2223/643* (2013.01)

(58) Field of Classification Search
    CPC ........... G01N 23/083; G01N 23/20083; G01N 23/207; G01N 23/04; G01N 2223/045; G01N 2223/637; G01N 23/20; G01N 23/201; G01N 2223/308; G01V 5/005; G01V 5/0016; G01V 5/0025; G01V 5/00; G01V 5/0041; G21K 1/02; G21K 2207/00; A61B 6/027; A61B 6/022; A61B 6/06; A61B 6/482; A61B 6/487; A61B 6/503; A61B 6/504; A61B 6/505; A61B 6/032; A61B 6/4028; A61B 6/4488; A61B 6/4014; A61B 6/4035; A61B 6/4241; A61B 6/4042; A61B 6/4085; A61B 6/4208; A61B 6/4233; A61B 6/4266; A61B 6/463
    USPC ..................... 378/4, 9, 10, 62, 119, 147–149
    See application file for complete search history.

(56) References Cited

U.S. PATENT DOCUMENTS

| | | | |
|---|---|---|---|
| 7,844,027 B2 | 11/2010 | Harding et al. | |
| 7,869,566 B2 | 1/2011 | Edic et al. | |
| 7,924,978 B2 | 4/2011 | Harding | |
| 8,477,904 B2 | 7/2013 | Blaj | |
| 2005/0128069 A1 | 6/2005 | Skatter | |
| 2006/0140340 A1 | 6/2006 | Kravis | |
| 2009/0003514 A1* | 1/2009 | Edic | G01V 5/0041 378/10 |
| 2009/0161817 A1 | 6/2009 | Schlomka | |
| 2010/0135462 A1 | 6/2010 | Harding et al. | |
| 2011/0188632 A1* | 8/2011 | Harding | G01V 5/0016 378/86 |
| 2012/0300901 A1 | 11/2012 | Lewalter et al. | |

FOREIGN PATENT DOCUMENTS

| | | |
|---|---|---|
| CN | 101821647 | 9/2010 |
| CN | 102253065 | 11/2011 |
| CN | 102483965 A | 5/2012 |
| CN | 203929678 | 11/2014 |
| JP | 2002-500766 A | 1/2002 |
| JP | 2003-513727 A | 4/2003 |
| JP | 2004-081870 A | 3/2004 |
| JP | 2007-530085 A | 11/2007 |
| JP | 2007-533993 A | 11/2007 |
| JP | 2008-501463 A | 1/2008 |
| JP | 2009-512851 A | 3/2009 |
| JP | 2010-190900 A | 9/2010 |
| JP | 2012-528332 A | 11/2012 |
| JP | 2014-000409 A | 1/2014 |
| JP | 2015-127705 A | 7/2015 |
| WO | WO 2005/121756 | 12/2005 |
| WO | WO 2010/138607 A1 | 12/2010 |
| WO | WO 2010/138607 A8 | 4/2012 |

OTHER PUBLICATIONS

Harding, G., et al., "Coherent X-ray scatter imaging and its applications in biomedical science and industry," Radiation Physics and Chemistry 56 (1999) 229-245 (17 pages).
International Search Report dated Oct. 27, 2016 in PCT Application No. PCT/CN2016/094460 (12 pages).
Office Action issued in corresponding CN application No. 201510958891.6, dated Jan. 23, 2019.
Office Action issued in JP application No. 2017-561701, dated Nov. 13, 2018.

* cited by examiner

MULTI-MODALITY DETECTION SYSTEM AND METHOD

CROSS REFERENCE TO RELATED APPLICATION(S)

This application is based upon and claims benefit/priority of Chinese Patent Application No. 201510958891.6, filed on Dec. 18, 2015, published as CN 106896120 A, which are incorporated herein by reference in entirety.

BACKGROUND

Technical Field

The present disclosure generally relates to a technical field of imaging, and more particularly to systems and methods for multi-modality detection.

Description of the Related Art

In current radiation imaging techniques, X-ray transmission imaging and X-ray diffraction imaging have become two common non-destructive testing methods. These two X-ray imaging techniques may be used separately, and may also be used in combination in order to improve detection accuracy.

With respect to the combined use of these two techniques, a two-stage detection system has been disclosed in U.S. Pat. No. 7,924,978B2 and U.S. Pat. No. 7,869,566B2. In such a two-stage detection system, a stage of X-ray Computed Tomography (CT) detection may be performed firstly, and then another stage of X-ray Diffraction (XRD) detection is performed. However, such a two-stage detection system actually is combined of two independent systems, each of which utilizes an independent radiation source. Thus, the system is bulky and the usage of the radiation source is low. Moreover, such a two-stage detection system needs to precisely control a position of a suspicious region between the two independent systems. Accordingly, the detection efficiency thereof will be relatively low.

Further, U.S. Pat. No. 7,787,591B2 discloses an inverse fan-beam XRD detection system in which a multi-angle transmission imaging can be performed at the same time of the XRD detection. Although this system only uses one set of radiation source, this system actually is a quasi-3D chromatographic detection system and the radiation source has a limited angle range, which makes it difficult to achieve an imaging quality same as that of the CT imaging technique.

OVERVIEW OF SOME ASPECTS

According to one aspect of the present disclosure, there is provided a multi-modality detection system, including: a distributed radiation source configured to irradiate an object under detection; a primary collimator configured to separate rays of the distributed radiation source into two parts, wherein one part is for CT detection and the other part is for XRD detection; a CT detection device configured to perform a CT detection to acquire a CT image of the object under detection; and an XRD detection device configured to perform an XRD detection to acquire an XRD image of the object under detection, wherein the CT detection and the XRD detection are performed simultaneously.

According to another aspect of the present disclosure, there is provided a multi-modality detection method, including: controlling a distributed radiation source to emit rays for irradiating an object being detected; forming, by a primary collimator, rays of the distributed radiation source into two parts, wherein one part is for CT detection and the other part is for XRD detection; performing, by a CT detection device, a CT detection to acquire a CT image of the object being detected; and performing, by a XRD detection device, a XRD detection to acquire a XRD image of the object being detected, wherein the CT detection and the XRD detection are performed simultaneously.

BRIEF DESCRIPTION OF THE DRAWINGS

Features and advantages of the present disclosure would be better understood by referring to the accompanying drawings. It is to be understood that the accompanying drawings are exemplary only, and are not restrictive of the present disclosure. In these drawings.

DETAILED DESCRIPTION OF ILLUSTRATIVE IMPLEMENTATIONS

In the following detailed description, numerous specific details are set forth in order to provide a thorough understanding of the present inventions/application. However, it is obvious to those skilled in the art that the present application can be practiced without some of the specific details. The embodiments described are merely examples, and the present application is not limited to the specific configurations and algorithms set forth in the example embodiments. However, the present application can cover various modification(s), replacement(s) and improvement(s) of elements, components and algorithms, without departing from the scope of the present inventions/application.

In the following, FIGS. 1-10 refer to and illustrate various multi-modality detection systems and methods according to embodiments of the present disclosure.

Figure 1:
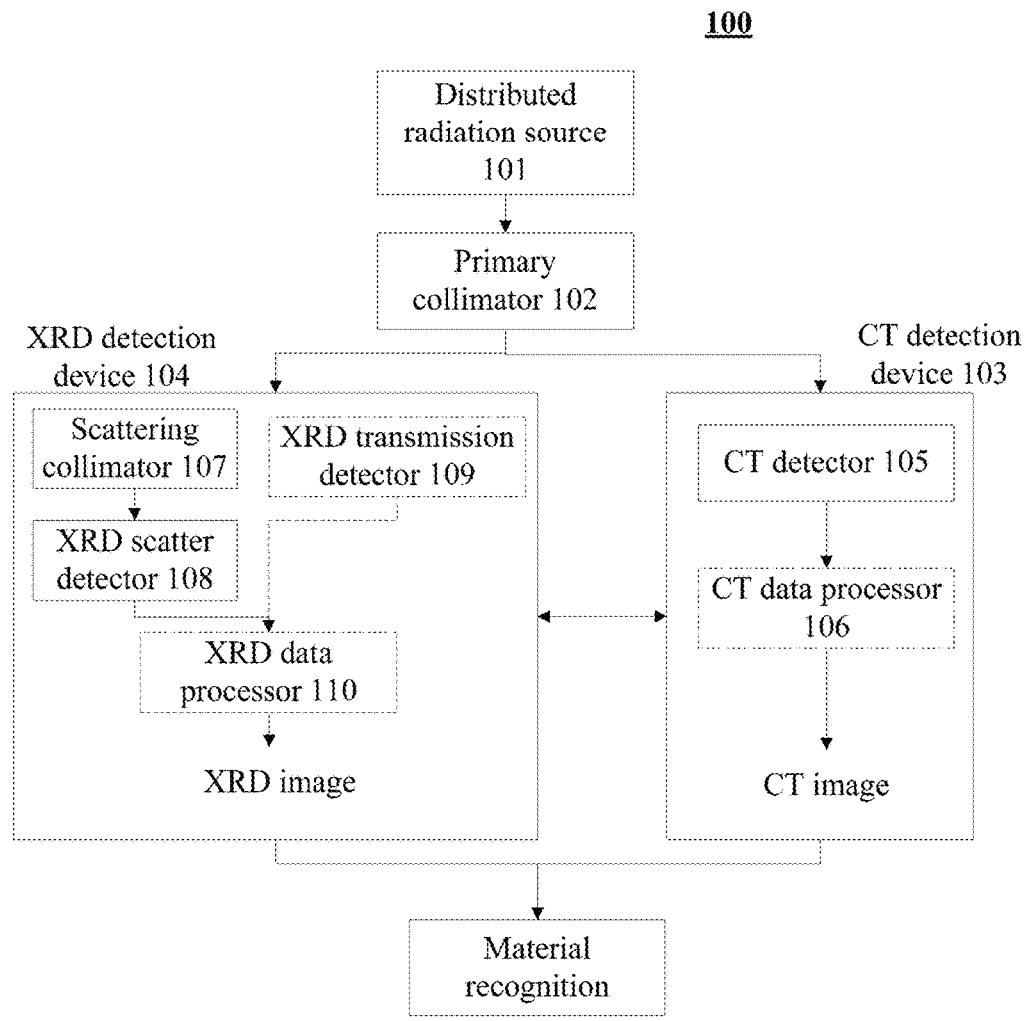
FIG. 1 is an example block diagram illustrating a multi-modality detection system consistent with embodiment(s) of the present disclosure.

FIG. 1 is an example block diagram illustrating a multi-modality detection system 100 according to an embodiment of the present disclosure. As shown in FIG. 1, the multi-modality detection system 100 of this embodiment may include: a distributed radiation source 101 configured to irradiate an object under detection; a primary collimator 102 configured to separate rays of the distributed radiation source 101 into two parts, wherein one part is for CT detection and the other part is for XRD detection; a CT detection device 103 configured to perform a CT detection to acquire a CT image of the object under detection; and an XRD detection device 104 configured to perform an XRD detection to acquire an XRD image of the object under detection, wherein the CT detection and the XRD detection are performed simultaneously.

In an embodiment, the primary collimator may be a primary collimator with two openings, so as to separate the rays of the distributed radiation source into two parts, in which one part is for CT detection and the other part is for XRD detection. However, it should be understood that such separation performed by the primary collimator in association with the rays of the distributed radiation source does not necessarily indicate splitting of the rays into two parts physically, but it is also feasible to form, by the primary collimator, a ray beam with a large cone angle, such that one part of the rays is used for CT detection and another part of the rays is used for XRD detection.

For the CT detection, the CT detection device 103 may include at least one CT detector 105 that performs the CT detection to acquire CT data.

In some embodiments, the CT detection device 103 may further include a CT data processor 106 that processes the CT data acquired by the CT detector 105 to obtain the CT image. Although the CT detector 105 and the CT data processor 106 are described herein as separate units, it is to be understood that these two units may be combined together. Alternatively, the CT detector 105 may transfer the CT data to a certain processing device external to the CT detection device 103 for processing, and the external processing device may then transfer the processed CT image back to the CT detection device 103.

In some embodiments, the CT detection device 103 may further include a scattering collimator (not shown in this figure). This scattering collimator may be arranged between the primary collimator 102 and the CT detector 105, and configured to control a direction of the rays for CT detection, in order to improve the CT imaging quality of the CT detection device 103. It should be understood that this scattering collimator is not necessary for the CT detection device 103.

For the XRD detection, it is to be understood that the rays for XRD detection will be scattered by the object under detection. In an embodiment, the XRD detection device 104 includes: a scattering collimator 107 configured to select, from scattered rays, rays having a same scattering direction; and at least one XRD scatter detector 108 configured to receive the rays having the same scattering direction through the scattering collimator 107, so as to obtain XRD scatter data.

Further, it should be understood that the rays for XRD detection may transmit through the object under detection. In an embodiment, the XRD detection device 104 may further includes at least one XRD transmission detector 109 configured to receive rays transmitted through the object under detection, so as to obtain XRD transmission data.

In some embodiments, the XRD detection device 104 may further includes an XRD data processor 110 that performs a processing for the XRD scatter data and the XRD transmission data to obtain the XRD image. Although the XRD scatter detector 108 and the XRD transmission detector 109 are described herein as separate units, it should be understood that they may be integrated together, which is similar to the above description associated with the CT detection. Alternatively, the XRD scatter detector 108 and/or the XRD transmission detector 109 may transfer the XRD data to a certain processing device external to the XRD detection device 104 for processing, and the processing device may then transfer the processed XRD image back to the XRD detection device 104.

The CT image obtained from the CT detection device 103 and the XRD image obtained from the XRD detection device 104 can be used for material recognition. Further, as shown in FIG. 1, the XRD detection device 104 and the CT detection device 103 can communicate data of the XRD image and CT image with each other to calibrate their respective data. Thereby, in accordance with the multi-modality detection system 100, the CT detection device 103 and the XRD detection device 104 can share a single set of distributed radiation source 101, and the CT detection and the XRD detection can be performed simultaneously.

Figure 2:
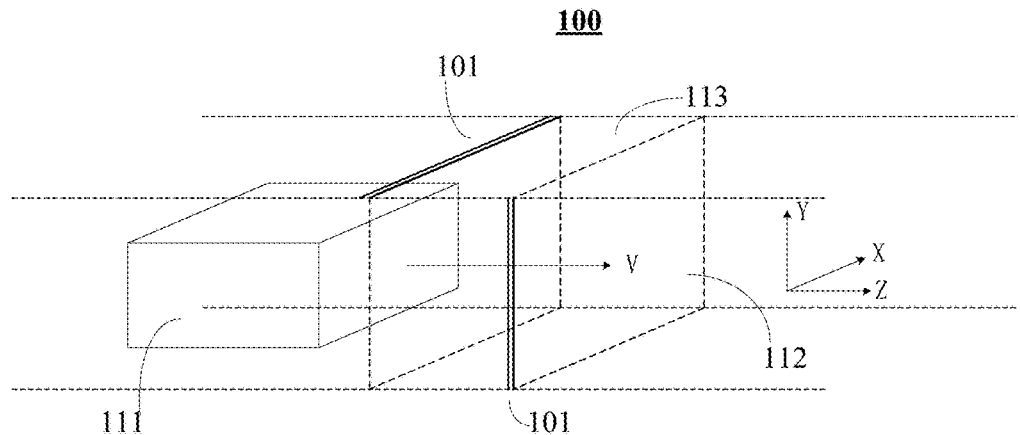
FIG. 2 is a schematic diagram illustrating a multi-modality detection system consistent with embodiment(s) of the present disclosure.

FIG. 2 is a schematic diagram illustrating a multi-modality detection system 100 according to an embodiment of the present disclosure. As shown in FIG. 2, the object under detection 111 travels with a conveyor belt towards a direction of Z in a limited speed of V, to pass through a transfer passage 112. It is to be noted that, a coordinate system of XYZ is introduced in FIG. 2 for the simplicity of description, in which the Z direction is the direction towards which the conveyor belt travels, Y direction is a direction vertical to the plane of the conveyor belt, and X direction is a direction vertical to a plane formed by Z and Y directions.

A multi-modality detection system 100 may include a distributed radiation source 101 configured to irradiate an object under detection 111. In FIG. 2, a number of the distributed radiation source 101 is shown as two, but it is to be understood that the multi-modality detection system 100 may include more distributed radiation sources 101. The distributed radiation source 101 may be positioned on at least a part of an internal side of a transfer passage frame structure 113. As shown in FIG. 2, one of these two distributed radiation sources 101 is located at a top edge of the internal side of the transfer passage frame structure 113, and another one is located at a side edge of the internal side of the transfer passage frame structure 113. Nevertheless, the positions of the distributed radiation sources 101 are not limited thereto, for example the distributed radiation sources 101 may be positioned at any position that is located on the internal side of at least one of a top, bottom, and side wall of the transfer passage frame structure 113.

There may be at least one radiation source focus point on the distributed radiation source 101, and such radiation source focus may be independently activated to emit rays. It is to be understood that the manner in which these radiation source focus points are activated (for example, the activation sequence and possible combinations) may be controlled by a distributed radiation source control device or a control program. Further, in a case of a plurality of distributed radiation sources 101, the plurality of distributed radiation sources 101 may have the same number of the radiation source focus points, or may have different number of the radiation source focus points. At any time during activation of the radiation source focus points on the distributed radiation source 101, the XRD data and the CT data can be acquired simultaneously.

The multi-modality detection system 100 may further include a primary collimator 102, a CT detection device 103, and an XRD detection device 104 (which are not shown in FIG. 2). The primary collimator 102 separates rays of the distributed radiation source 101 into two parts, in which one part is for CT detection and the other part is for XRD detection. The CT detection device 103 performs a CT detection to acquire a CT image of the object under detection; and an XRD detection device 104 performs an XRD detection to acquire an XRD image of the object under detection. Notably, the CT detection and the XRD detection are performed simultaneously.

In the multi-modality detection system of the present disclosure, where there exists a plurality of distributed radiation sources, the system includes a plurality of primary collimators, CT detection devices and XRD detection devices corresponding to the plurality of distributed radiation sources respectively. With respect to each distributed radiation source, the primary collimator is arranged between that distributed radiation source and the object under detection, and the CT detection device and XRD detection device are arranged such that the object under detection is positioned between the primary collimator and the CT detection device and XRD detection device. That is to say, the CT detection device and the XRD detection device are arranged on a side of the object under detection, which is opposite to the primary collimator. For example, referring to FIG. 2, one distributed radiation source 101 is positioned at the top edge of the internal side of the transfer passage frame structure 113, the primary collimator may be deployed below the distributed radiation source 101 to separate the rays, while the CT detection device and the XRD detection device may be arranged below the conveyor belt.

As described above, in such multi-modality detection system(s) 100 consistent with embodiments of the present disclosure, a CT detection system and an XRD detection system are integrated together, and thus the traditional multi-stage detections can be organically combined into a single stage. Moreover, the CT detection system and XRD detection system are substantially sharing a single set of distributed radiation source, and thus the CT image and XRD image can be acquired simultaneously. Therefore, compared with a multi-stage detection system, the system footprint can be reduced and the detection efficiency and accuracy can be improved.

Figure 3:
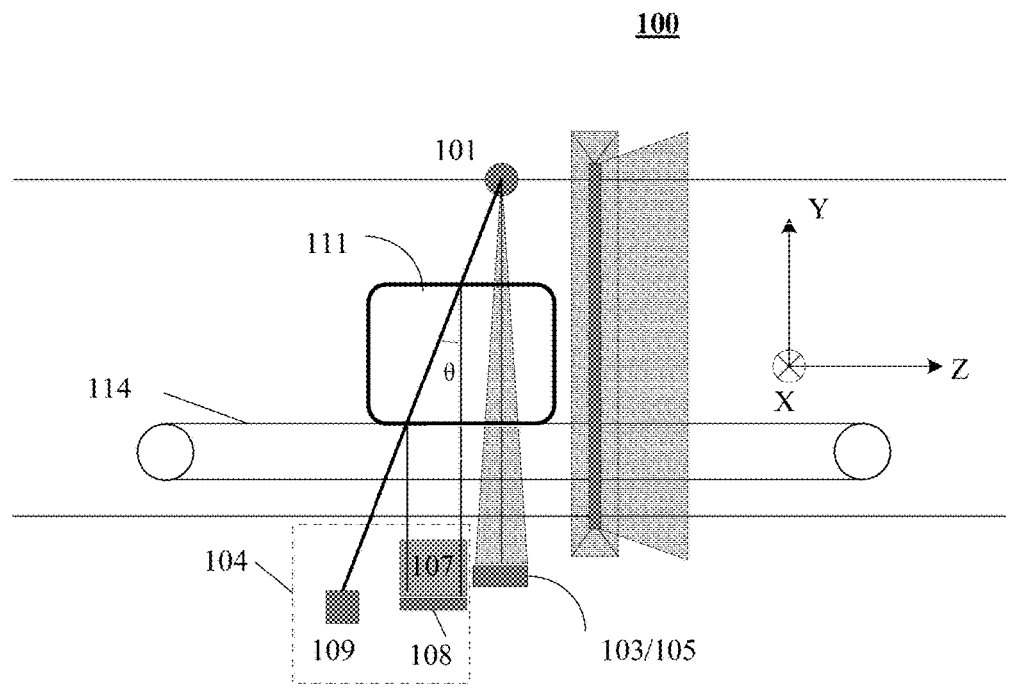
FIG. 3 is a longitudinal section diagram illustrating a multi-modality detection system consistent with embodiment(s) of the present disclosure.

FIG. 3 is a longitudinal section diagram illustrating a multi-modality detection system 100 according to an embodiment of the present disclosure. A coordinate system of XYZ, which is same as the coordinate system of FIG. 2, is also introduced into FIG. 3. Since FIG. 3 is a longitudinal section diagram, the X direction is oriented vertically to the inside of the paper plane. Further, similar reference numbers (callouts) within FIG. 3 and FIG. 1 refer to like elements. It is to be understood that the following discussions are described only with respect to one distributed radiation source. In the case of a plurality of distributed radiation sources, a primary collimator, a CT detection device, and an XRD detection device will be deployed for each distributed radiation source, and such detections will be performed similarly for each distributed radiation source.

As shown in FIG. 3, an object under detection 111 travels with a conveyor belt 114 towards Z direction. When passing through a transfer passage 112, the object 111 will be irradiated by a distributed radiation source 101. As shown in FIG. 3, rays emitted from radiation source focus points on the distributed radiation source 101 will be separated into two parts, in which one part transmits towards a CT detection device 103 for CT detection, and the other part transmits towards an XRD detection device 104 for XRD detection. The above separation of the rays is completed substantially by a primary collimator 102 arranged between the distributed radiation source 101 and the object 111. There may exist a certain angle between radiation planes of these two parts of rays separated by the primary collimator 102, such that the XRD detection and the CT detection do not interfere with each other. Accordingly, the CT detection and XRD detection can be performed independently and simultaneously. A detection plane for XRD detection may exist along one side or both sides of a CT detection plane.

As shown in FIG. 3, for the CT detection, the multi-modality detection system 100 includes a CT detection device 103. The CT detection device 103 includes at least one CT detector 105 that performs the CT detection to acquire CT data. In an embodiment, the CT detector 105 may be selected from one of the following detectors: an energy deposition detector, a dual energy detector, or an energy resolving detector (i.e., photon counting detector). The CT detector 105 may be one of the following types of detectors: one-dimension line array detector, or two-dimension plane array detector, and the two-dimension plane array detector may be for example a plane detector or a camber detector. The CT detection device 103 may further include a CT data processor 106 (not shown in this figure) that processes the CT data acquired by the CT detector 105 to obtain the CT image. The rays for CT detection may form a fan-beam or a cone-beam, which respectively correspond to single-slice or multi-slice spiral CT imaging approaches.

For XRD detection, the multi-modality detection system 100 includes an XRD detection device 104. After passing through the primary collimator 102, the rays for XRD detection will be scattered upon irradiating to the object 111. As shown in FIG. 3, the scattered rays will pass through a scattering collimator 107 and enter into at least one XRD scatter detector 108 included in the XRD detection device 104. The scattering collimator 107 selects from the scattered rays, rays having a same scattering direction. The at least one XRD scatter detector 108 receives the rays having the same scattering direction through the scattering collimator 107, so as to obtain XRD scatter data. In FIG. 3, the scattering collimator 107 will select scattered rays having a scattering angle of θ to enter into the at least one XRD scatter detector 108. In an embodiment, the XRD scatter detector 108 may be a pixelated energy resolving detector.

Further, the rays for XRD detection may partially transmit through the object 111. Therefore, in an embodiment, the XRD detection device may further include an XRD transmission detector 109 configured to receive rays transmitted through the object 111, so as to obtain XRD transmission data. The obtained XRD transmission data can be used to calibrate measurement results of the XRD scatter detector 108 to have more thoughtful and accurate information of the object 111.

Figure 4:
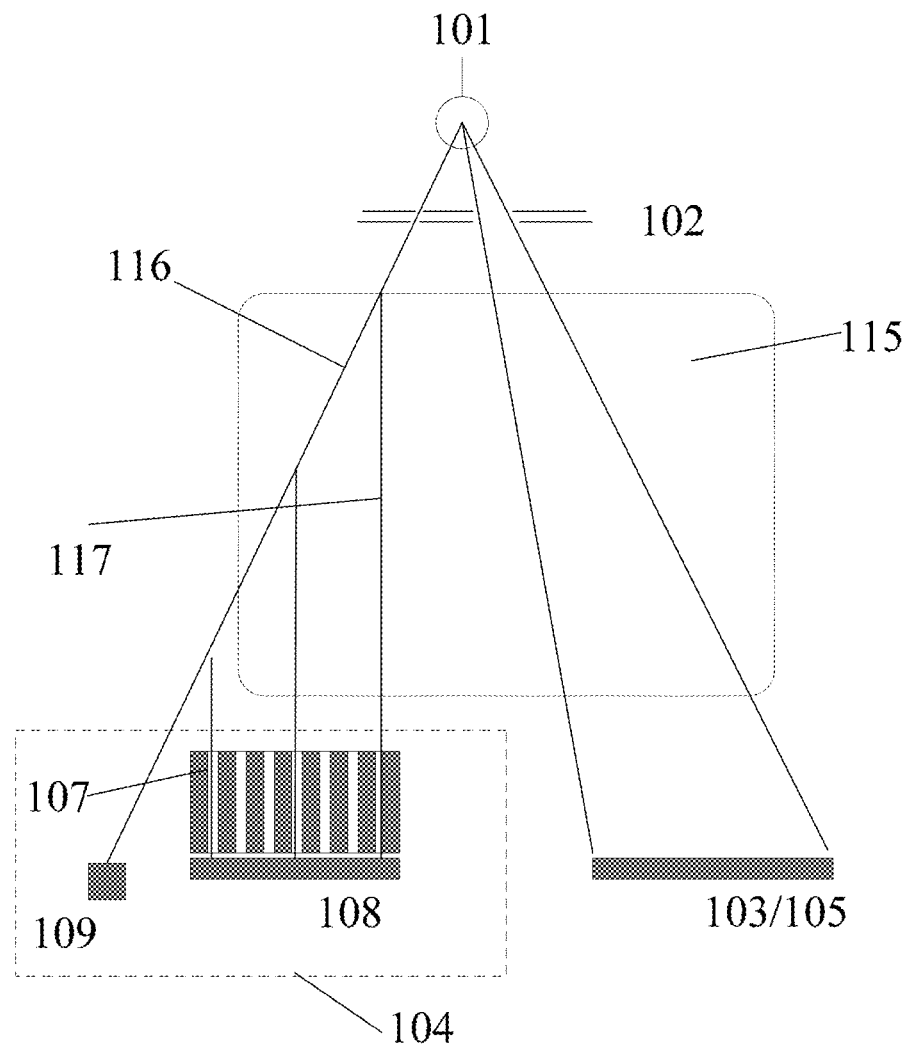
FIG. 4 is a schematic diagram illustrating the multi-modality imaging principle consistent with embodiment(s) of the present disclosure.

FIG. 4 is a schematic diagram illustrating the multi-modality imaging principle according to embodiments of the present disclosure. Reference numbers (callouts) in FIG. 4 that are the same as in FIGS. 1 through 3 refer to the same elements. As shown in FIG. 4, the reference sign 115 indicates a detection region. Rays transmitted from radiation source focus points on a distributed radiation source 101 will be separated by the restriction of a primary collimator 102 into two parts, in which one part transmits towards a CT detection device 103 for CT detection, and the other part transmits towards an XRD detection device 104 for XRD detection. There may exist a certain angle between radiation planes of these two parts of rays separated by the primary collimator 102, such that the XRD detection and the CT detection do not interfere with each other. Accordingly, the CT detection and XRD detection can be performed independently and simultaneously.

Figure 5:
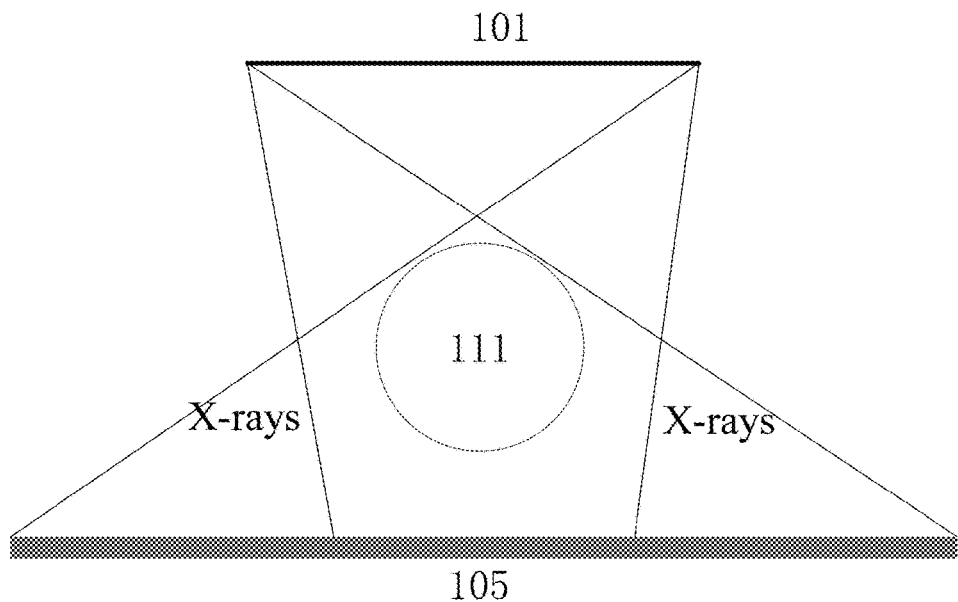
FIG. 5 is a schematic diagram illustrating the CT imaging principle consistent with embodiment(s) of the present disclosure.

For the CT detection, a CT detector 105 included in the CT detection device 103 receives part of rays separated by the restriction of the primary collimator 102 to perform the CT detection to acquire CT data. FIG. 5 is a schematic diagram illustrating the CT imaging principle according to an embodiment of the present disclosure. As shown in FIG. 5, an object under detection 111 is located between a distributed radiation source 101 and the CT detector 105. As described above, the rays for CT detection may form a fan-beam or a cone-beam, which respectively correspond to single-slice or multi-slice spiral CT imaging approaches. When different radiation source focus points on the distributed radiation source 101 are activated or lightened, rays transmitted from the radiation source focus points may irradiate the object 111 from different angles. By intercepting a radiation plane, the CT detector 105 may obtain projection data on the radiation plane. FIG. 5 only shows an exemplary imaging situation where rays transmitted from radiation source focus points at two edge positions of the distributed radiation source 101 pass through the object 111. It should be understood that, when more radiation source focus points on the distributed radiation source 101 are activated, the projection image will reflect the status of the object 111, itself, more accurately.

Figure 6:
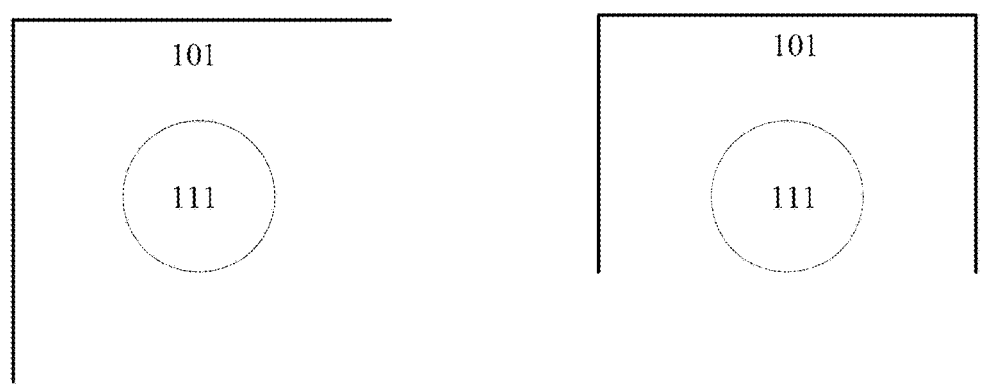
FIG. 6 is a schematic diagram illustrating a distributed radiation source arranged in L-type and U-type consistent with embodiment(s) of the present disclosure.
Figure 7:
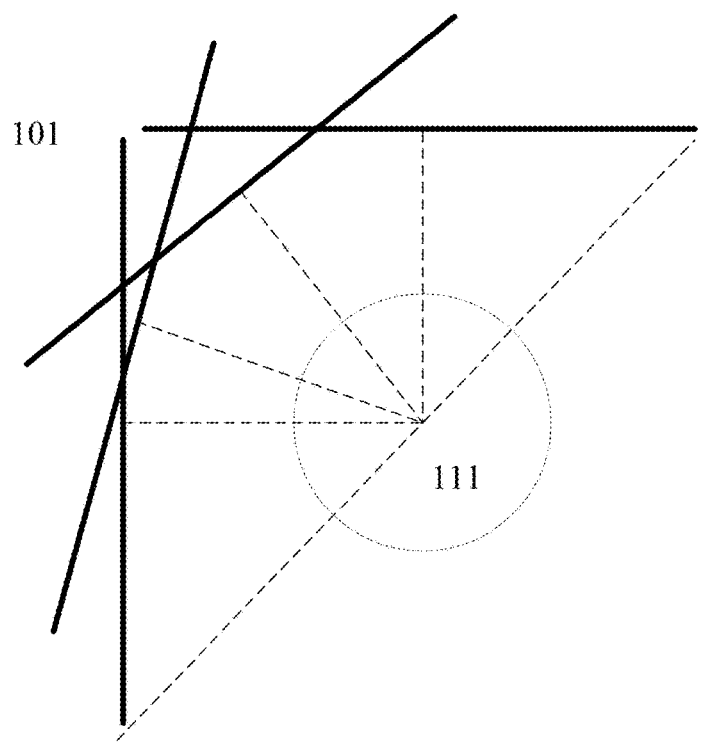
FIG. 7 is a schematic diagram illustrating a distributed radiation source arranged in multi-segment type consistent with other embodiment(s) of the present disclosure.

In FIG. 5, the distributed radiation sources 101 are shown as being arranged in a linear pattern. Nevertheless, the arrangement of the distributed radiation source 101 is not limited thereto, and in alternative embodiments, the distributed radiation sources 101 may be arranged in Arc type, L-type, U-type, or other types. For example, the distributed radiation sources 101 may be consisted of multiple segments distributed on different planes, i.e., a multi-segment type. FIG. 6 shows distributed radiation sources arranged in L type and U type, which can ensure that projection data cover a very large angle range, so as to improve the accuracy of the CT image reconstruction. FIG. 7 shows a distributed radiation source module arranged in the multi-segment type, which can obtain projection data of enough angle range.

Continuing to refer to FIG. 4, on the other hand, an XRD detection device 104 receives the other part of rays separated by the restriction of the primary collimator 102 to perform the XRD detection to acquire XRD image. As shown in FIG. 4, rays 116 for XRD detection will be scattered upon irradiating to the object under detection. It should be understood that there are scatted rays of several different directions, but the system is configured to select, by a scattering collimator 107, from the scattered rays, rays having a same scattering direction to enter into at least one XRD scatter detector 108 included in the XRD detection device 104. By receiving rays being restricted by the scattering collimator 107, the at least one XRD scatter detector 108 performs the XRD detection so as to obtain XRD scatter data (for example, XRD scattering energy resolving diagram).

The XRD detection is capable of point by point measurement. Therefore, with respect to various arrangement types of the distributed radiation sources, a complete set of data can be obtained for the XRD detection. As the CT detection requires a large amount of radiation source focus points with small spaces and a wide distribution, XRD detection may use all or a part of these radiation source focus points, and by introducing respective rays from the primary collimator, obtains, with the restriction of the scattering collimator, scattering data of a certain scattering angle at respective points.

Figure 8:
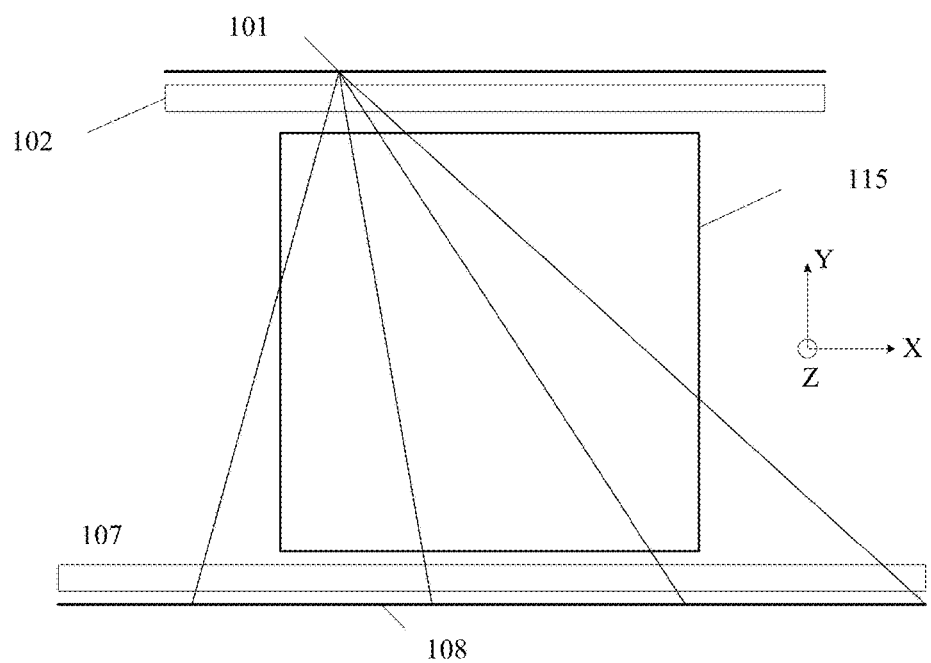
FIG. 8 is a schematic diagram illustrating form and distribution of ray beams for XRD detection consistent with embodiment(s) of the present disclosure.
Figure 9:
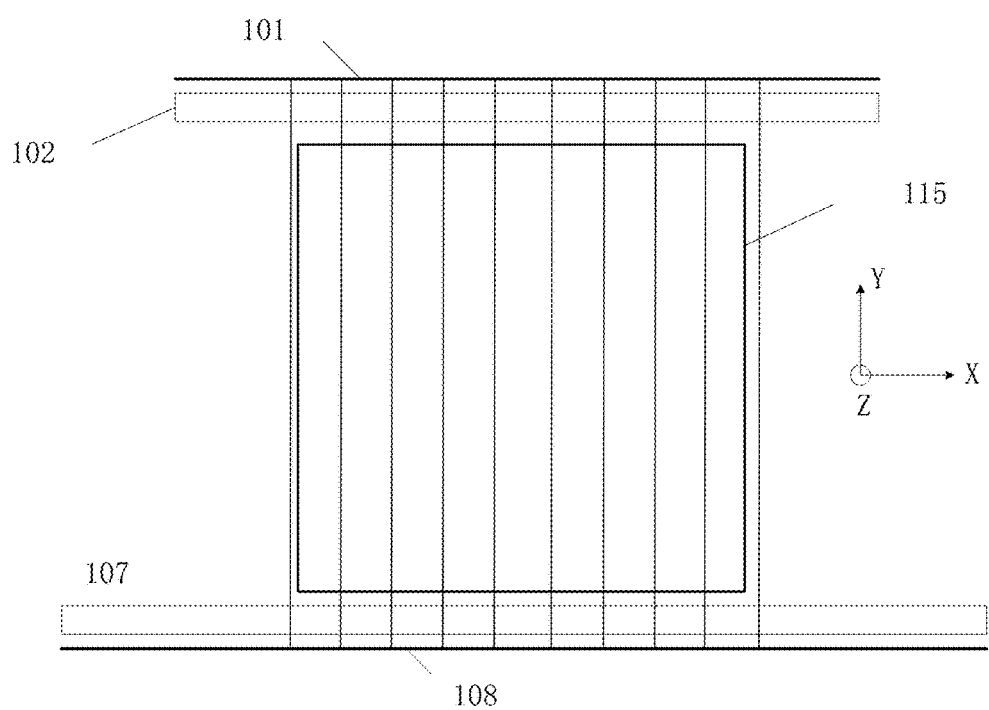
FIG. 9 is a schematic diagram illustrating form and distribution of ray beams for XRD detection consistent with other embodiment(s) of the present disclosure.

FIG. 8 is a schematic diagram illustrating form and distribution of ray beams for XRD detection according to an embodiment of the present disclosure. A coordinate system of XYZ, which is same as the coordinate system of FIG. 2, is also introduced into FIG. 8, and the X direction is also oriented vertically to the inside of the paper plane. As shown in FIG. 8, under the restriction of the primary collimator 102, each radiation source focus point on a distributed radiation source 101 transmits a plurality of pencil-beam rays, and these pencil-beam rays are distributed as a fan. FIG. 9 is a schematic diagram illustrating a form and distribution of ray beams for XRD detection according to another embodiment of the present disclosure. A coordinate system of XYZ, which is same as the coordinate system of FIG. 8, is also introduced into FIG. 9, and the X direction is also oriented vertically to the inside of the paper plane. As shown in FIG. 9, under the restriction of the primary collimator 102, each radiation source focus point on a distributed radiation source 101 transmits one pencil-beam ray, and pencil-beam rays transmitted from all radiation source focus points are distributed in parallel. No matter how the rays are distributed, with the restriction of the scattering collimator 107, these ray beams will then inject into respective XRD scatter detector 108, such that each XRD scatter detector 108 measures scattering information of a fixed scattering angle from each point on the object under detection. It should be understood that the rays for XRD detection are not limited to the above description.

Further, as shown in FIG. 4, the rays for XRD detection may transmit through the object under detection. Therefore, the XRD detection device 104 may further include an XRD transmission detector 109 configured to receive rays transmitted through the object, so as to obtain XRD transmission data (e.g., XRD transmission energy resolving diagram). The obtained XRD transmission data can be used to calibrate measurement results of the XRD scatter detector 108 to have more thoughtful and accurate information of the object.

It is to be noted that there may exist a certain angular relationship between a radiation plane of rays for XRD detection and another radiation plane of rays for CT detection, such that the XRD detection and the CT detection may be better separated. This angle may vary depending on requirements. In an embodiment, the radiation plane of rays for CT detection may be parallel to a XY plane (i.e., vertical to the travelling direction of the conveyor belt), while the central radiation plane of rays for XRD detection may have a certain angle with respect to the XY plane. Further, a detection plane for XRD detection may exist along one side or both sides of a CT detection plane.

Figure 10:
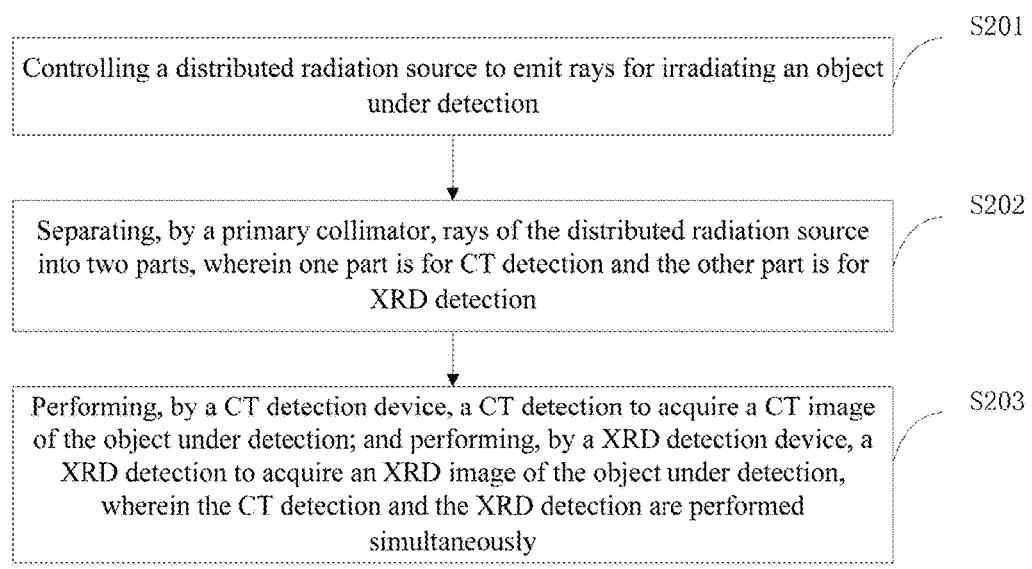
FIG. 10 is a flow diagram illustrating a multi-modality detection method consistent with exemplary embodiment(s).

The multi-modality detection system is illustrated above in accordance with the embodiments of the present disclosure. The present disclosure also provides a multi-modality detection method. FIG. 10 provides a flow diagram illustrating a multi-modality detection method 200 according to an exemplary embodiment. As shown in FIG. 10, the multi-modality detection 200 includes: S201, controlling a distributed radiation source to emit rays for irradiating an object under detection; S202, separating, by a primary collimator, rays of the distributed radiation source into two parts, wherein one part is for CT detection and the other part is for XRD detection; S203, performing, by a CT detection device, a CT detection to acquire a CT image of the object under detection, and, performing, by an XRD detection device, an XRD detection to acquire an XRD image of the object under detection, wherein the CT detection and the XRD detection are performed simultaneously.

According to the multi-modality detection systems and methods of the embodiments of the present disclosure, the CT detection device and the XRD detection device may communicate data of CT image and data of XRD image with each other to calibrate their respective data. Specifically, the XRD image usually has low Signal To Noise Ratio (SNR) and low spatial resolution. Thereby, a situation of overlapped XRD spectrums of different materials may occur at edges of the object under detection. In contrast, the CT image has clear structure information and high spatial resolution. Accordingly, data of the CT image may be used to sharp the edge of the XRD image. This can prevent, to some extent, error recognition of a material caused by overlapped spectrums.

Figure 11:
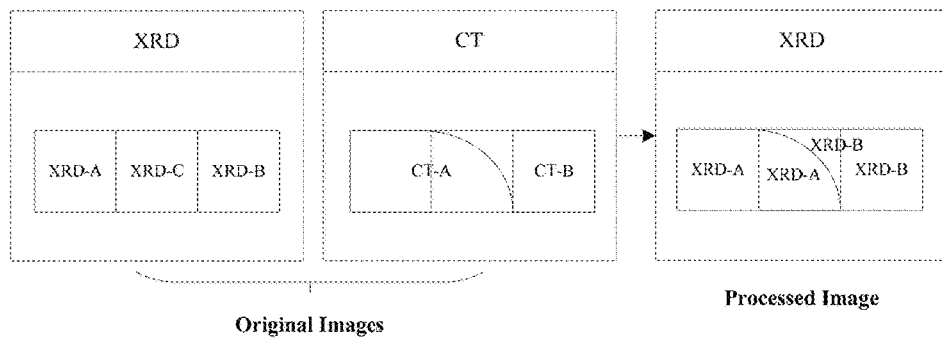
FIG. 11 is a schematic diagram of using CT data to calibrate an XRD image consistent with exemplary embodiment(s).

FIG. 11 is a schematic diagram of using CT data to calibrate an XRD image according to an exemplary embodiment. Specifically, due to the low spatial resolution of the XRD image, it is likely that one pixel in an XRD image will be truly presented as an edge between two materials in a CT image. At this time, by weighted summation of independent XRD spectrums of these two materials and comparing the weighted summation result with XRD image information of this pixel point which may be located at the material edge, it is determined that the XRD image information of this pixel point is a summation of XRD image information of two materials, rather than another third material. After that, XRD information of these two materials may be filled into their respective structures, and thus the overlapped XRD data can be removed.

Alternatively, image data obtained from the XRD detection can be used to calibrate the CT image. Specifically, an overall distribution of coherent scattering and incoherent scattering of each point from the object (mostly, coherent scattering) can be obtained through the XRD detection. By the use of the XRD spectrum of each point, a scattering kernel function for the materials within a certain range may be obtained, which can be used to perform scattering calibration for the CT image, so as to improve the accuracy of the CT image data.

Moreover, information of the CT image and XRD image can be combined with image structure similarity (CT image) and physical material similarity (XRD image) to perform weight calculation according to a Non-Local denoising algorithm. Thus, image denoising can be performed on these two images to improve the SNR of their respective images.

Furthermore, if the CT image is measured by an energy resolving detector with high resolution, the distribution of an attenuation coefficient versus energy for each point on the object can be obtained. These CT data may be used to perform attenuation calibration on the XRD image. Compared with traditional attenuation calibration approaches such as using an attenuation spectrum of a transmission path to replace an attenuation spectrum of the scattering path, the attenuation calibration described herein has better accuracy and also the transmission detector used in the XRD detection can be removed.

As described above, in accordance with the multi-modality detection systems and methods of the embodiments of the present disclosure, the material recognition can be performed based on the combination of material information obtained from both these two detections (i.e., CT detection and XRD detection). Systems and methods according to the embodiments of the present disclosure can use the CT detection information and XRD detection information together and simultaneously, rather than an approach of "CT first, XRD second" to perform the material recognition. Accordingly, a region that is regarded as a safe region by the CT detection will also be detected by XRD detection, and thus both the false positive rate and the false negative rate can be decreased.

Furthermore, the multi-modality detection systems and methods of the embodiments of the present disclosure substantially and organically combine the CT detection system and the XRD detection system together, in terms of the system structure and physical information. These two systems share a single set of distributed radiation source, which reduces the system cost and meanwhile decreases volume of the whole detection system. The CT detection and XRD detection are performed simultaneously and their detection planes are closed. Thereby, it may reduce complexity of position alignment and multiple interactions between multi-modality information, and also improve detection efficiency and accuracy of the system. In the system, both the CT detection and the XRD detection belong to stationary measurements, which avoid complex mechanical movements of the detectors, radiation sources, and the object under detection and thus improve stability of the system. In addition, data of the CT detection and the XRD detection are processed simultaneously. This simultaneous processing increases information exchange between the multi-modality data, makes the integration of the system truly achieved from the outside (system structure) to inside (data), and thus improves the detection quality.

It should be understood that the multi-modality detection systems and methods of the embodiments of the present disclosure may be applied in the field of security detection. However, those skilled in the art would understood that the multi-modality detection system and method in accordance with the embodiments of the present disclosure are not limited to the field of security detection, but may also be applied in other relevant fields.

It is to be noted that terms "comprising" or "comprises" in the claims do not exclude an element or component that is not listed in the claims. An article "a" or "an" positioned before an element or component also does not exclude the existence of multiple such element or component.

Further, it is to be noted that the language used in the specification has been principally selected for readability and instructional purposes, and it may not have been selected to delineate or circumscribe all of the inventive subject matter. Therefore, a plurality of amendments and variations will be apparent to those skilled in the art without departing from the scope and spirit of the present inventions and appended claims. Accordingly, the disclosure of the above embodiments of the invention is intended to be illustrative, but not limiting, of the scope of the invention. It is intended that the scope of the invention only be limited by the appended claims.

What is claimed is:

1. A multi-modality detection system, comprising:
   a distributed radiation source configured to irradiate an object under detection;
   a primary collimator configured to separate rays of the distributed radiation source into two parts, wherein one part is for CT detection and the other part is for XRD detection;
   a CT detection device configured to perform a CT detection to acquire a CT image of the object under detection; and an XRD detection device comprising at least one XRD transmission detector and configured to perform an XRD detection to acquire an XRD image of the object under detection, wherein the CT detection and the XRD detection are performed simultaneously, and wherein the XRD detection device and the CT detection device communicate data of the XRD image and CT image with each other to calibrate their respective data.

2. The multi-modality detection system of claim 1, wherein the multi-modality detection system comprises a plurality of distributed radiation sources, and further comprises a primary collimator, a CT detection device and an XRD detection device corresponding to each of the plurality of distributed radiation sources.

3. The multi-modality detection system of claim 2, wherein each of the plurality of distributed radiation sources is positioned on at least a part of an internal side of a transfer passage frame structure, and for each of the plurality of distributed radiation sources, the primary collimator is arranged between the distributed radiation source and the object under detection, and the CT detection device and XRD detection device are arranged such that the object under detection is positioned between the primary collimator and the CT detection device and XRD detection device.

4. The multi-modality detection system of claim 2, wherein each of the plurality of distributed radiation sources is selected from one of the following types: linear type, arc type, L-type, U-type, and multi-segment type.

5. The multi-modality detection system of claim 2, wherein each of the plurality of distributed radiation sources has multiple radiation source focus points, and these radiation source focus points are independently activated to emit rays.

6. The multi-modality detection system of claim 5, further comprising a distributed radiation source control device which controls the manner in which the radiation source focus points on each of the plurality of distributed radiation sources are activated.

7. The multi-modality detection system of claim 5, wherein the plurality of distributed radiation sources have different or the same number of the radiation source focus points.

8. The multi-modality detection system of claim 1, wherein the CT detection device comprises at least one CT detector that performs the CT detection to acquire CT data, and wherein the CT detector is selected from one of the following detectors: an energy deposition detector, a dual energy detector, or an energy resolving detector.

9. The multi-modality detection system of claim 8, wherein the CT detection device further comprises a CT data processor that processes the CT data acquired by the CT detector to obtain the CT image.

10. The multi-modality detection system of claim 1, wherein the rays for the CT detection form a fan-beam or a cone-beam.

11. The multi-modality detection system of claim 1, wherein the rays for the XRD detection are scattered by the object under detection, and wherein the XRD detection device comprises:

a scattering collimator configured to select, from scattered rays, rays having a same scattering direction;

at least one XRD scatter detector configured to receive the rays having the same scattering direction through the scattering collimator, so as to obtain XRD scatter data.

12. The multi-modality detection system of claim 11, wherein the rays for the XRD detection transmit through the object under detection, and wherein:

the at least one XRD transmission detector is configured to receive rays transmitted through the object under detection, so as to obtain XRD transmission data.

13. The multi-modality detection system of claim 12, wherein the XRD detection device further comprises an XRD data processor that processes the XRD scatter data and the XRD transmission data to obtain the XRD image.

14. The multi-modality detection system of claim 1, wherein the rays for the XRD detection form pencil beams.

15. The multi-modality detection system of claim 14, wherein the rays for the XRD detection are distributed in a fan or in parallel.

16. The multi-modality detection system of claim 1, wherein the one part of the rays are divided into multiple portions, which are respectively used for the XRD detection.

17. The multi-modality detection system of claim 1, wherein the other part of the rays are divided into multiple portions, which are respectively used for the CT detection.

18. The multi-modality detection system of claim 1, wherein a radiation plane of the rays for the CT detection has a certain angle with respect to a central radiation plane of the rays for the XRD detection, the angle is determined such that the XRD detection and the CT detection do not interfere with each other.

19. A method for multi-modality detection, the method comprising:

controlling a distributed radiation source to emit rays for irradiating an object under detection;

separating, by a primary collimator, rays of the distributed radiation source into two parts, wherein one part is for CT detection and the other part is for XRD detection;

performing, by a CT detection device, a CT detection to acquire a CT image of the object under detection; and performing, by an XRD detection device, an XRD detection to acquire an XRD image of the object under detection, wherein the XRD detection device comprises at least one XRD transmission detector, wherein the CT detection and the XRD detection are performed simultaneously, and wherein the XRD detection device and the CT detection device communicate data of the XRD image and CT image with each other to calibrate their respective data.

* * * * *